US00PP30165P3

(12) United States Plant Patent
Danziger

(10) Patent No.: US PP30,165 P3
(45) Date of Patent: Jan. 29, 2019

(54) ***CALIBRACHOA* PLANT NAMED 'DCALCORANG'**

(50) Latin Name: ***Calibrachoa* hybrid**
Varietal Denomination: DCALCORANG

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/731,166

(22) Filed: Apr. 26, 2017

(65) Prior Publication Data

US 2018/0317362 P1 Nov. 1, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./263.1, 413
See application file for complete search history.

(56) References Cited

PUBLICATIONS

Malmborg's Greenhouse Spring 2017. https://issuu.com/erin2350/docs/2017_catalog_online. Accessed Jun. 8, 2018. 4 pages.*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Calibrachoa* cultivar named 'DCALCORANG' is disclosed, characterized by a semi-trailing growth habit. The plants flower early and abundantly. The flower color is a dark, vivid orange and plants are day length neutral in flowering. The new variety is a *Calibrachoa*, normally produced as an outdoor garden or container plant.

2 Drawing Sheets

Figure 1:
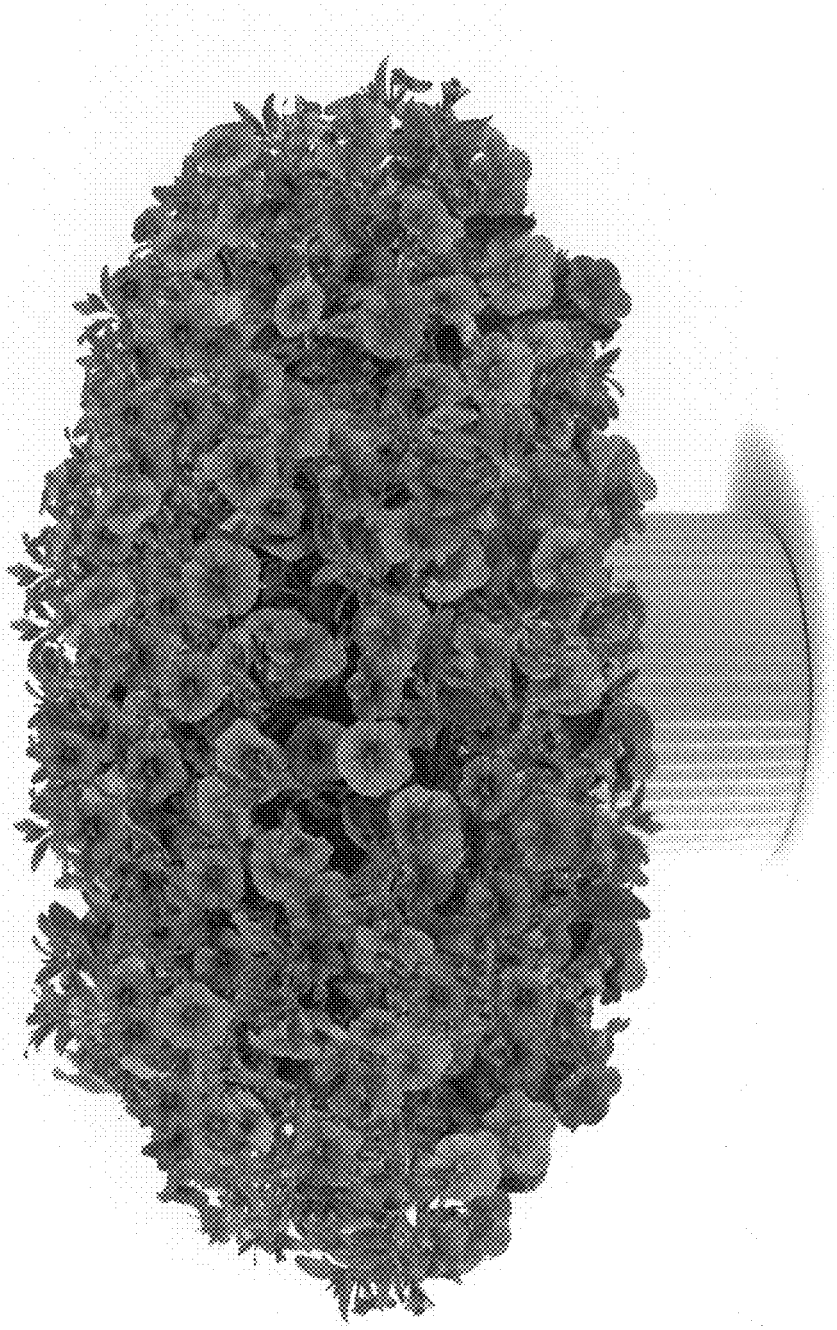

Latin name of the genus and species: *Calibrachoa* hybrid.
Variety denomination: 'DCALCORANG'.

BACKGROUND OF THE INVENTION

The new *Calibrachoa hybrida* cultivar is a product of a planned breeding program conducted by the inventor, Gavriel Danziger in Moshav Mishmar Hashiva, Israel. The objective of the breeding program was to produce new *Calibrachoa* varieties for commercial ornamental purposes with novel production characteristics. The cross resulting in this new variety was made during April of 2014.

The seed parent is the unpatented, propriety variety referred to as *Calibrachoa* 'cv. Z-440'. The pollen parent is the unpatented, propriety variety referred to as *Calibrachoa* 'cv. 12-3093'. The new variety was discovered in November of 2014 by the inventor in a group of seedlings resulting from the 2014 crossing, in a greenhouse in Moshav Mishmar Hashiva, Israel.

Asexual reproduction of the new cultivar 'DCALCORANG' was first performed by terminal vegetative cuttings at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DCALCORANG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALCORANG' These characteristics in combination distinguish 'DCALCORANG' as a new and distinct *Calibrachoa* cultivar:

1. Early flowering.
2. Abundant flowering.
3. Day length neutral flowering.
4. Vivid dark orange flowers.
5. Semi-trailing plant habit.

PARENT COMPARISON

Plants of the new cultivar 'DCALCORANG' are similar to plants of the seed parent, *Calibrachoa* 'cv. Z-440' most horticultural characteristics, however, plants of the new cultivar 'DCALCORANG' differ in the following;

1. The seed parent is much more vigorous then the new variety.
2. The new variety flowers much earlier than the seed parent.
3. The seed parent has a light orange flower color, the new variety has a darker orange flower.
4. The seed parent has a more open plant habit than the new variety.

Plants of the new cultivar 'DCALCORANG' are similar to plants of the pollen parent, *Calibrachoa* 'cv. 12-3093' most horticultural characteristics however, plants of the new cultivar 'DCALCORANG' differ in the following;

1. The pollen parent has a trailing growth habit, the new variety has a semi-trailing habit.
2. The new variety produces more branches per plant than the pollen parent.
3. The pollen parent has a light red flower color, the new variety has a dark orange colored flower.
4. The new variety flowers abundantly, the pollen parent flowers moderately.

COMMERCIAL COMPARISON

Plants of the new cultivar 'DCALCORANG' can be compared to the unpatented commercial variety *Calibrachoa* 'DANOA476'. These varieties are similar in most horticultural characteristics; however, 'DCALCORANG' differs in the following:

1. 'DCALCORANG' is flowers earlier then 'DANOA476'.
2. 'DCALCORANG' is day length neutral the comparison variety is not.
3. 'DCALCORANG' has dark orange flower, the comparable variety has light orange flowers
4. The comparable variety is much more vigorous then 'DCALCORANG'.

Plants of the new cultivar 'DCALCORANG' can also be compared to the commercial variety 'Calipetite Red Improved', patent status unverified. These varieties are similar in most horticultural characteristics; however, 'DCALCORANG' differs in the following:

1. 'DCALCORANG' flower is dark orange, 'Calipetite Red Improved' is red.
2. 'DCALCORANG' has a larger flower than the comparison variety.
3. 'DCALCORANG' is more vigorous than the comparison variety.

BRIEF DESCRIPTION OF THE PHOTOGRAPHS

The accompanying photograph in FIG. 1 illustrates in full color a typical plant of 'DCALCORANG' grown in a greenhouse, in Moshav Mishmar Hashiva, Israel.

Figure 2:
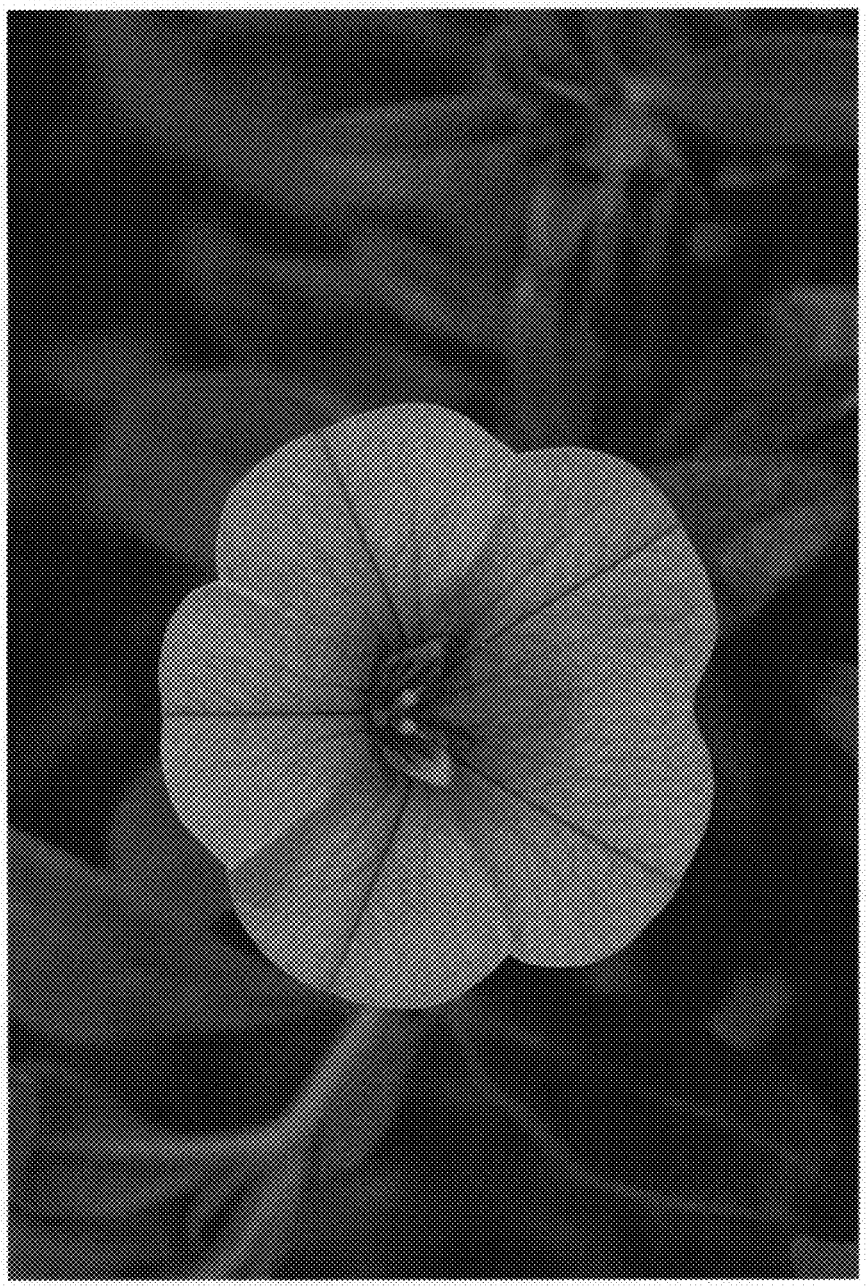

FIG. 2 illustrates in full color a typical mature flower of 'DCALCORANG' during Spring. Age of the plant photographed is approximately 60 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALCORANG' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 15° C. to 28° C. during the days, 15° C. to 20° C. during the nights. Measurements and numerical values represent averages of typical plant types.

Botanical classification: *Calibrachoa* hybrid 'DCALCORANG'.

PROPAGATION

Typical method: Terminal vegetative cuttings.
Time to initiate roots: About 10-15 days at approximately 18° C.
Root description: Fibrous. Colored tan and white, not accurately measured with R.H.S. chart.

PLANT

Growth habit: Semi-trailing.
Pot size of plant described: 13 cm.
Height: To top of flowers: 9 cm.
Plant spread: 40-50 cm.
Growth rate: Medium.
Branching characteristics:
Length of primary lateral branches: About 20 cm.
Diameter of lateral branches: About 0.3 cm.
Quantity of primary lateral branches: 4.
Characteristics of primary lateral branches:
*Form*.—Cylindrical.
*Diameter*.—About 0.3 cm.
*Color*.—Near Yellow-Green 146 C.
*Texture*.—Scabrous.
*Strength*.—Good.
*Internode length*.—About 1.5 cm.

FOLIAGE

Leaf:
*Arrangement*.—Alternate.
*Quantity*.—Approximately 40 per branch.
*Average length*.—2.8 cm.
*Average width*.—1.1 cm.
*Shape of blade*.—Elliptic.
*Apex*.—Rounded.
*Base*.—Acuminate.
*Margin*.—Entire.
*Texture of top surface*.—Glabrous.
*Pubescence*.—Scabrous.
*Aspect*.—90 degrees.
*Color*.—Young foliage upper side: 137B RHS. Young foliage under side: 147B RHS. Mature foliage upper side: N137B RHS. Mature foliage under side: 147B RHS.
*Venation*.—Type: Pinnate. Venation color upper side: 137A RHS. Venation color under side: 147B RHS.
*Petiole*.—Length: 1 to 2 mm. Diameter: 1 mm. Color: Near Green N137B RHS. Texture: Glabrous.

FLOWER

Natural flowering season: All seasons.
Days to flowering from rooted cutting: About 20-30 days.
Inflorescence and flower type and habit: Individual salver-form flowers. Outwardly facing.
Rate of flower opening: 2 to 3 days from bud to fully opened flower.
Flower longevity on plant: 4 to 7 days.
Approximate quantity of flowers per plant: About 70.
Persistent or self-cleaning: Self-cleaning.

Bud:
*Shape*.—Ovoid.
*Length*.—0.2 0.3 cm.
*Diameter*.—0.15 cm.
*Color*.—Yellow-Green 145CRHS.

Flower size:
*Diameter*.—3.5-4 cm.
*Length*.—3.5-4 cm.
*Flower tube diameter at distal end*.—0.3 cm.
*Flower tube diameter at proximal end*.—1.1 cm.

Petals:
*Length from throat*.—1.5 to 2.0 cm.
*Width*.—1.8 to 2.0 cm.
*Quantity*.—5.
*Texture*.—Glabrous.
*Apex*.—Rounded.
*Margin*.—Entire.

Color:
*When opening*.—Upper surface: Near Red 44B and Red 46B, both colors present. Lower surface: Near Orange-Red 35C with Red-Purple 61A veins.
*Fully opened*.—Upper surface: Near Red 42B and 44A, both colors present. Lower surface: Near Orange-Red 35C with 61A veins. Flower throat (inside): Near Yellow 10A. Flower throat, vein: Near Red 46C. Flower tube (outside): Near Yellow 8B. Flower tube, vein: Near Red 46A. Petal color, fading to: Near Orange N25A with Red 42A.

Calyx/sepals:
*Quantity per flower*.—5.
*Shape*.—Lance-Shaped (lanceolate).
*Length*.—1.5 cm.
*Width*.—0.4 cm.
*Apex*.—Rounded.
*Base*.—Cuneate.
*Margin*.—Entire.
*Texture*.—Glabrous.
*Color*.—Upper Surface: Near Yellow-Green 147B. Lower Surface: Near Yellow-Green 147C.

Peduncle: Not Present.

Pedicel:
*Length*.—2 to 2.5 cm.
*Diameter*.—0.1 cm.
*Color*.—Near Yellow-Green 147C.
*Orientation*.—45 degrees from branch.

Fragrance: None.

REPRODUCTIVE ORGANS

Stamens:
*Number*.—5.
*Filament length*.—0.8 to 1.3 cm.

Anthers:
*Length*.—0.15 cm.
*Shape*.—Globose.
*Color*.—Near Yellow 9C.
*Pollen*.—Color: Near Yellow 6C. Quantity: Scant.

Pistil:
*Number*.—1.
*Length*.—1.2 cm.
*Style*.—Length: 0.9 cm. Color: Near Green 138C.
*Stigma*.—Shape: Oblate. Color: Near Green 138A. Ovary Color: Near Yellow-Green 145B.

OTHER CHARACTERISTICS

Seeds and fruits: About 30 Brown, rounded seeds of about 0.5 mm diameter, per one brown, conical capsule. Capsule light brown, seeds dark brown, neither accurately measured with R.H.S. chart.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.

Temperature tolerance: 5° C. to 30° C.

Drought tolerance: No tolerance for drought.

What is claimed is:

1. A new and distinct cultivar of *Calibrachoa* plant named 'DCALCORANG' as herein illustrated and described.

* * * * *